United States Patent [19]

Straub et al.

[11] Patent Number: 4,574,802
[45] Date of Patent: Mar. 11, 1986

[54] SURGICAL INSTRUMENT FOR CUTTING TISSUE, IN PARTICULAR CARTILAGE

[75] Inventors: Reinhold Straub, Schramberg; Eugen Eberhard, Mülheim, both of Fed. Rep. of Germany

[73] Assignee: Ewald Hensler, Immendingen, Fed. Rep. of Germany

[21] Appl. No.: 575,992

[22] Filed: Feb. 1, 1984

[30] Foreign Application Priority Data

Feb. 2, 1983 [DE] Fed. Rep. of Germany ....... 3303335

[51] Int. Cl.⁴ ............................................. A61F 17/32
[52] U.S. Cl. ................................................ 128/305
[58] Field of Search ................ 128/305, 318; 433/159; 30/240, 29.5

[56] References Cited

U.S. PATENT DOCUMENTS 4,499,899 2/1985 Lyons ................................. 128/305

Primary Examiner—Robert Peshock
Attorney, Agent, or Firm—Leonard Bloom

[57] ABSTRACT

In a surgical instrument for cutting tissue and having a jaw part that comprises a stationary, U-shaped curette and a cutting part which is secured on a rotating rod rotatably supported in a tube carrying the curette, the rotating rod is according to the invention supported rotatably at both sides of the cutting part on the legs of the curette. As a result, it is possible to exert strong cutting forces without impairing the geometry of the cutting edges as a consequence of deformation of the rotating rod.

4 Claims, 2 Drawing Figures

SURGICAL INSTRUMENT FOR CUTTING TISSUE, IN PARTICULAR CARTILAGE

FIELD OF THE INVENTION

The invention relates generally to a surgical instrument for cutting tissue, in particular cartilage. The instrument has a jaw part comprising a fixed, U-shaped curette that is secured to a tube connected to a handle part, with the legs of the U being oriented toward the axis of the tube, and a cutting part that can be moved into the open inside face of the curette. The cutting part is secured to a rotating rod that is disposed coaxially in the tube and is rotatable by means of an actuating handle.

BACKGROUND OF THE INVENTION

Surgical instruments of this type are used for cutting through tissues that offer resistance, such as cartilage. In particular, such instruments are used for severing the cartilage of the meniscus. In a known surgical instrument of this type (Rotary Basket Punch, by Acufex Microsurgical, Inc., Boston, Mass.), the U-shaped curette, which acts as the stationary cutting part, is secured to the tube with the end of one of the legs of the U. The ends of the two legs of the U are connected with one another via a crosspiece, by means of which the end of the leg of the U remote from the tube is also connected with the tube. The movable cutting part is mounted on the end of the rotating rod that protrudes freely out of the tube. To generate the cutting movement, an actuating handle is moved toward a stationary handle part connected with the tube, whereupon the actuating handle rotates the rotating rod relative to the tube.

If strong cutting forces are exerted with this known instrument, as must necessarily be done to sever the meniscus cartilage, for instance, which is up to 4 mm thick, then the geometry of the cutting edges becomes deformed, particularly in the vicinity of the leg of the U remote from the tube, because the free end of the rotating rod supporting the cutting part and the leg of the U of the curette remote from the tube, which is supported only by the connecting crosspiece, are forced apart from one another.

OBJECT AND SUMMARY OF THE INVENTION

It is accordingly a principal object of the present invention to improve a surgical instrument of this general type such that it is possible to exert stronger cutting forces with it. This object is attained in accordance with the invention by providing that the rotating rod protrudes axially outward beyond the cutting part and is supported in a sleeve in axial alignment with the tube and provided on the leg of the U of the curette remote from the tube.

Advantageous exemplary embodiments and further developments of the invention are disclosed in the dependent claims.

In the surgical instrument according to the invention, the rotating rod carrying the cutting part is not free at its front end but is instead rotatably supported in a sleeve provided on the curette. Supporting the rotating rod at both sides of the cutting part prevents deflection of the rotating part and thus of the cutting part, even if strong cutting forces are being exerted in the course of severing resistant tissues, such as cartilage. In particular, an accurate reciprocal guidance of the cutting edges of the curette and the cutting part over the entire circumference of the cutting part is assured in that the supports of the rotating rod at either side of the cutting part, that is, the tube on one side and the sleeve on the other, are firmly connected to the legs of the U of the curette.

Furthermore, supporting the rotating rod in the sleeve attached to the leg of the curette that is remote from the tube renders the connecting crosspiece between the ends of the U legs of the curette of the known instrument superfluous. The rotating rod itself acts as a support for the free legs of the U of the curette. The space between the U legs of the curette can therefore remain open, so that the pivoting angle of the cutting part, and hence the opening angle of the jaw part, is not restricted.

The cutting part is advantageously curved in concave fashion from its cutting edge toward its center. The result is a sharper cutting edge, which is adapted to the higher cutting pressure that can be exerted with the jaw part according to the invention. Furthermore, as a result of this embodiment of the cutting part the severed tissue is pushed toward the middle of the jaw part and thus carried away from the site of the cutting, and this has a favorable effect on the conditions for cutting.

The invention will now be described in greater detail in terms of an exemplary embodiment, shown in the drawings.

DESCRIPTION OF THE PREFERRED EMBODIMENT

Figure 1:
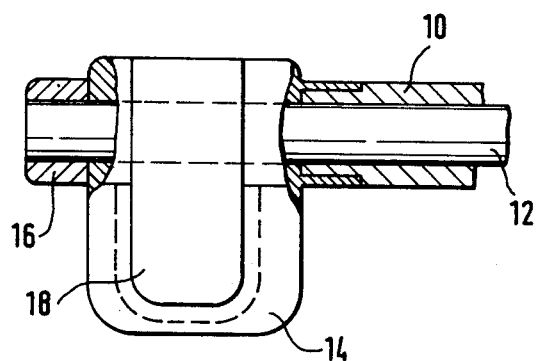
FIG. 1 shows the jaw part of a surgical instrument in a side view that has been partially cut away axially.

The jaw part, which is shown in the drawing on a scale of 5:1, is disposed on a surgical instrument that is not shown and is not the subject of the invention. This surgical instrument has a stationary handle part to which a tube 10 is attached. An actuating handle is supported such that it is movable counter to the fixed handle part; via a suitable mechanism, its movement is converted into a rotational movement of a rotating rod 12 supported coaxially and rotatably in the tube 10.

A curette 14 is attached to the front end of the tube 10, being mounted for instance by means of a connection piece onto the tube 10 and soldered thereto. The curette 14 has the shape of an open U, the legs of which are oriented toward the axis of the tube 10. The end of one leg of the U of the curette 14 is secured to the tube 10 and has a bore matching the inside cross section of the tube 10, through which bore the rotating rod 12 passes.

The end of the other leg of the U has a corresponding bore, which is in alignment with the first bore and thus in axial alignment with the tube. A sleeve 16 is provided on the outside on this leg of the U remote from the tube 10; it is in axial alignment with the bores of the U legs and the tube 10 and is for instance soldered to the curette 14. The rotating rod 12 extends with its front end into the sleeve 16 and is rotatably supported therein.

Between the two U legs of the curette 14, a cutting part 18 is seated on the rotating rod 12, being connected in a rotationally fixed manner thereto, preferably being soldered to the rotating rod 12. As shown in FIG. 1, the cutting part 18 corresponds in its dimensions with the open inner face of the curette 14, so that upon the rotation of the rotating rod 12 this cutting part can be moved all the way through the curette 14. As a result, the inner edge of the curette 14 and the outer edge of the cutting part 18 come into engagement with one another, as cutting edges.

In order to maintain an accurately cutting engagement of the cutting edges of the cutting part 18 and the curette 14, which upon the clockwise rotation of the cutting part 18 in FIG. 1 are oriented toward one another, the inner opening cross section of the curette 14 widens with increasing distance from the cutting edge, as indicated by dashed lines in the drawing. The cutting part 18, at its circumferential face, recedes somewhat, beginning at the cutting edge.

Figure 2:
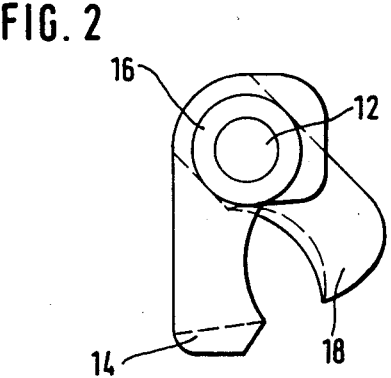
FIG. 2 is an end view of the jaw part.

As shown in dashed lines in FIG. 2, the face of the cutting part 18 that during the cutting process is oriented toward the curette is curved concavely toward its center point, beginning at the cutting edge. As a result of this curvature of the cutting part and because of a bevel extending from the cutting edge of the curette 14, both cutting edges are embodied in the shape of a wedge, as a result of which the severed tissue is pushed away to either side during cutting.

What is claimed is:

1. A surgical instrument for cutting tissue, in particular cartilage, having a jaw part comprising a stationary U-shaped curette, which is secured to a tube connected to a handle part, its U legs being oriented toward the axis of the tube, and a cutting part movable into an open inner face of the curette, the cutting part being secured on a rotating rod that is disposed coaxially in the tube and is rotatable; the improvement including a sleeve and wherein said rotating rod protrudes axially beyond said cutting part and is supported in said sleeve, which is in axial alignment with the tube and is provided on that leg of the U of the curette remote from the tube.

2. An improved surgical instrument as defined by claim 1, wherein said curette is open between ends of legs of said U-shaped curette.

3. An improved surgical instrument as defined by claim 1, wherein said cutting part is curved in concave fashion from its cutting edge toward its center point.

4. An improved surgical instrument as defined by claim 1, wherein said cutting part is curved in concave fashion from its cutting edge toward its center point.

* * * * *